United States Patent
Lemann

(10) Patent No.: US 6,203,807 B1
(45) Date of Patent: Mar. 20, 2001

(54) COSMETIC COMPOSITION WITH A LIPOPHILIC CONTINUOUS PHASE CONTAINING A NOVEL PIGMENT

(75) Inventor: Patricia Lemann, Creteil (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/438,051

(22) Filed: Nov. 10, 1999

(30) Foreign Application Priority Data

Nov. 10, 1998 (FR) .................................................. 98-14160

(51) Int. Cl.[7] ............................ A61K 7/00; A61K 7/025; A61K 33/24; A01N 59/16
(52) U.S. Cl. ............................ 424/401; 424/64; 424/646; 424/653
(58) Field of Search ............................... 424/61, 401, 63; 106/415

(56) References Cited

U.S. PATENT DOCUMENTS 5,273,577   12/1993   Liedek et al. ........................ 106/479
5,411,586 * 5/1995   Schmid et al. ........................ 106/415
5,993,834 * 11/1999  Shah et al. ............................ 424/401

FOREIGN PATENT DOCUMENTS 33 15 850   10/1984   (DE) .
0 551 637    7/1993   (EP) .
0 632 110    1/1995   (EP) .

* cited by examiner

Primary Examiner—Thurman K. Page
Assistant Examiner—Blessing Fubara
(74) Attorney, Agent, or Firm—Oblon, Spivak, McClelland, Maier & Neustadt, P.C.

(57) ABSTRACT

A cosmetic composition having a lipophilic continuous phase, in particular make-up compositions, containing a novel yellow pigment of intense, saturated color, which does not generate free radicals. This novel pigment is a bismuth vanadate of formula $BiVO_4$. By means of this pigment, it is possible to reduce the production of free radicals in the composition, when it is applied to the skin, the lips and the superficial body growths, and thus protect them. It also makes it possible to conserve the gloss of the films deposited.

16 Claims, No Drawings

COSMETIC COMPOSITION WITH A LIPOPHILIC CONTINUOUS PHASE CONTAINING A NOVEL PIGMENT

BACKGROUND OF THE INVENTION

1. Field of the Invention

The present invention relates to cosmetic compositions with a lipophilic continuous phase, containing a novel yellow pigment of intense, saturated color which does not generate free radicals, and more especially to make-up compositions for the skin both of the human face and body, the lips and superficial body growths such as the nails, the eyelashes, the eyebrows or the hair.

2. Discussion of the Background

Make-up compositions, such as free or compact powders, foundations, face powders, eye shadows, lipsticks, concealers, blushers, mascaras, eyeliners, lip pencils or eye pencils or make-up products for the body, consist of a suitable vehicle and coloring agents of various natures, intended to give these compositions a certain color, before and/or after applying them to the skin, the lips and/or the superficial body growths.

These coloring agents can be lakes, inorganic or organic pigments and/or pearlescent pigments, or, alternatively, dyes. In the range of yellow pigments, cosmeticians have available pigments of inorganic origin such as yellow iron oxides and pigments of organic origin. Inorganic pigments, and in particular inorganic oxides, have the advantage of being relatively stable, but have the drawback of giving rather dull, pale colors. Organic lakes have the advantage of giving the compositions lively colors, but are mostly unstable with respect to light, temperature or pH. Some of these lakes also have the drawback of leaving unsightly marks on the skin or the nails after application, by running of the dye. As for pearlescent pigments, they allow varied, but never intense, colors to be obtained, with iridescent effects, but these are usually fairly weak.

Moreover, certain coloring agents have the drawback of generating free radicals in make-up formulations, thus modifying the yield of the colors and the stability of the compositions, and then on the skin after application, which promotes ageing of the skin (appearance of wrinkles, fine lines and yellowing of the skin). In particular, yellow iron oxides often give rise to an oxidation of polyunsaturated oils (for example plant oils), which limits the range of compositions. Examples of coloring agents which exhibit this drawback, include the yellow iron oxide mixtures (CI: 77492) sold under the trade name "Sicovit Yellow 10 E 172" by BASF, pigments of organic origin, and the aluminium lake of tartrazine on alumina (20/80) (CI: 19140, Cl: 77002) sold under the trade name FD & C Yellow 5 by Warner Jenkinson.

At the present time, to overcome this drawback, antioxidants such as ethoxyquine, for example, are used. Unfortunately, it is often difficult to find an antioxidant which is 100% effective given the multitude of ingredients present in make-up compositions. Furthermore, the antioxidants themselves often generate degradation products (oxidation of the antioxidant) which can cause interference.

SUMMARY OF THE INVENTION

It is an object of the present invention to provide a composition suitable for topical application, of a novel yellow pigment of intense, saturated color.

It is another object of the invention to provide a composition suitable for topical application which is stable and which has the advantage of generating far fewer free radicals than the pigments conventionally used, in particular, for obtaining a yellow color.

It is another object of the present invention to provide methods of treating various parts of the body, e.g., the skin, to take advantage of the properties of the inventive composition.

Surprisingly, the inventors have found that bismuth vanadate of formula $BiVO_4$ allows the production of free radicals to be limited, since it has the property of generating very few free radicals, and thus allows the use of antioxidants in the compositions to be limited. In addition, this pigment makes it possible to obtain an intense coloration and in particular a very bright, intense lemon-yellow color of very great color purity, which does not run on keratin substances and is stable with respect to light, pH and temperature. In addition, it broadens the color range in the cosmetics field and participates in the creation of vivid greens by mixing bright oranges with blues. Furthermore, it reduces the amount of pigments of the prior art, thus making it possible to preserve the sheen of the composition as well as that of the film deposited, which is highly desired for make-up products for the lips.

Thus, the objects of the present invention, and others, may be accomplished with a colored composition suitable for topical application, comprising a lipophilic continuous phase and an amount of bismuth vanadate effective to color the composition.

The objects of the present invention may also be accomplished with a method of preparing the inventive composition, comprising combining the lipophilic continuous phase and the bismuth vanadate.

The objects of the present invention may also be accomplished with a method of caring for the skin and/or the lips and/or the superficial body growths comprising, applying the inventive composition to the skin and/or the lips and/or the superficial body growths.

The objects of the present invention may also be accomplished with a method of making up the skin and/or the lips and/or the superficial body growths, comprising applying the inventive composition to the skin and/or the lips and/or the superficial body growths.

The objects of the present invention may also be accomplished with a method of protecting the skin and/or the lips and/or the superficial body growths, comprising applying the inventive composition to the skin and/or the lips and/or the superficial body growths.

The objects of the present invention may also be accomplished with a method of protecting the skin and/or the lips and/or the superficial body growths against the harmful effects of free radicals, comprising applying the inventive composition to the skin and/or the lips and/or the superficial body growths.

The objects of the present invention may also be accomplished with a method of alleviating the signs of ageing of the skin, comprising applying the inventive composition to the skin.

A more complete appreciation of the invention and many of the attendant advantages thereof will be readily obtained as the same becomes better understood by reference to the following detailed description.

DETAILED DESCRIPTION OF THE INVENTION

The manufacture of this pigment is, in particular, that described in documents EP-A-551,637 and EP-A-632,110. It has, in particular, a size of about 0.3 $\mu$m.

Bismuth vanadate can crystallize in various forms and thus express different yellow tones:

monoclinic lattice; fergusonite: bright yellow, density 6.959 tetragonal lattice; zircon: pale yellow, density 6.127 tetragonal lattice; scheelite: bright yellow, density 6.929 orthorhombic lattice; pulcherite: pale yellow.

It may also be in pure form or in a form deposited on a substrate. Preferably, it is in pure form and is sold under the reference Sicopal Gelb L1100 by BASF.

To demonstrate bismuth vanadate's property of not generating free radicals, an ethylene test has been conducted according to the process described in the article "Ethylene formation from methionine as a method to evaluate oxygen free radical scavenging and metal inactivation by cosmetics" by J. B. Galey, F. Millecamps and Q.-L. Nguyen, *International Journal of Cosmetic Science*, 13, 65–78, 1991, incorporated herein by reference.

The object is to compare the behavior of the inorganic pigment according to the invention with that of conventional pigments in a photo-oxidation test using iron as free-radical generator.

In the ethylene test measurement procedure, the $FeCl_3$ used to activate the production of free radicals was replaced with each of the pigments to be tested. The results are given in the table below.

| Dye | Ethylene Produced (peak area) | | |
|---|---|---|---|
| Concentration | 0.01% | 0.1% | 0.2% |
| Yellow iron oxide (CI: 77492) | 13,500 | 30,000 | 50,000 |
| Bismuth vanadate | 5000 | 5500 | 5000 |

The control $FeCl_3$ at 0.005% is on average 9000 (arbitrary unit—relative measurement).

In this test, the higher the amount of ethylene, the greater the production of free radicals.

Yellow iron oxide (CI: 77492) is not inert. At low dose, it activates up to a certain concentration at which the protective effect of the pigment comes into play, whereas for bismuth vanadate, the degree of ethylene produced is very low and does not change as a function of the concentration. This pigment may thus be used advantageously in make-up compositions and colored antisun compositions intended in particular for protecting the skin and/or mucous membranes such as the lips, without generating free radicals and thus limiting the degradation of the skin and/or the lips.

Compared with the yellow iron oxides commonly used in cosmetics, the pigment in the composition of the present invention also has the advantage of being more saturated with color, more vivid and of a more intense color, which makes it possible, in particular, to use it in smaller amounts, for an equivalent color yield. The calorimetric parameters of bismuth vanadate sold by BASF under the trade name Sicopal Gelb L 1100 relative to those of yellow iron oxide (CI: 77492) are given below:

| Parameter | Yellow iron oxide | Bismuth vanadate |
|---|---|---|
| L | 69.9 | 92.8 |
| a | 6.85 | −12.92 |
| b | 50.35 | 84.64 |
| c | 50.6 | 85.27 |

The higher the value of c, the more saturated the color: bismuth vanadate has a more vivid, more intense color than iron oxide, thus allowing a cosmetic composition to be strongly colored with a small amount of pigment. Thus, the theological problems (difficulty of application, non-uniform make-up effect) associated with an excessively large amount of pigments in the compositions of the prior art are largely attenuated.

Compared with an organic lake, bismuth vanadate gives better coverage for an equal amount of pigment.

The pigment according to the invention can be incorporated into a cosmetic or dermatological composition containing a lipophilic continuous phase, in particular a make-up composition, in an amount which can readily be determined by a person skilled in the art on the basis of his or her general knowledge, and which can range, for example, from 0.01 to 50% by weight relative to the weight of the composition, preferably in an amount ranging from 0.5 to 25% by weight. These ranges include all specific values and subranges therebetween, such as 0.02, 0.1, 0.2, 1, 2, 5, 10, 20, 30 and 40% by weight. Even at high concentration, this pigment does not destructure the composition.

The composition of the invention can be in the form of a product to be applied to the lips, the eyes, the skin and/or the superficial body growths of human beings. It therefore contains a cosmetically acceptable medium, i.e. a medium which is compatible with all keratin substances, such as the skin both of the human body and face, the nails, the hair, the eyelashes and the eyebrows.

According to the invention, this medium contains a lipophilic continuous phase, i.e. a mixture of one or more fatty substances or organic solvents which are immiscible with water, which can be liquid, pasty or solid at room temperature (25° C. in general). In particular, this medium can comprise or can be, in particular, in the form of a suspension, dispersion or solution in an oily or lipophilic organic solvent phase, which is optionally thickened, or even gelled; a suspension or dispersion in a waxy phase; a water-in-oil (W/O) emulsion or a multiple (W/O/W) emulsion, in the form of a cream, a paste or even a solid; an anhydrous gel or an oily foam; an emulsified gel; a two-phase or multiphase lotion; a spray, a free, compact or cast powder; an anhydrous paste. A person skilled in the art can select the appropriate pharmaceutical form, as well as the method for preparing it, on the basis of his or her general knowledge, given, on the one hand, the nature of the constituents used, in particular their solubility in the support, and, on the other hand, the application envisaged for the composition.

The composition thus comprises a lipophilic continuous phase which can contain fatty substances that are liquid at room temperature and atmospheric pressure, often referred to as oils, water-immiscible organic solvents, waxes, gums, pasty fatty substances or a mixture of these constituents. This continuous phase can represent from 0.5 to 99.99% of the total weight of the composition. This range includes all specific ranges and subranges therebetween, such as 1, 2, 5, 10, 25, 50, 75, 80, 90, 95 and 98% by weight.

When the composition according to the invention is in the form of an emulsion, it can also optionally comprise a surfactant, preferably in an amount of from 0 to 30% and, preferably, from 0.01 to 30% by weight relative to the total weight of the composition. These ranges include all specific values and subranges therebetween, including 0.02, 0.1, 0.5, 1, 2, 5, 10, 15, 20 and 25% by weight.

Depending on the application envisaged, the composition can also comprise a film-forming polymer (such as polyurethanes, polyacrylics, polyurethane and polyacrylic hybrids, polyesters, nitrocellulose, hydrocarbon-based resins and/or silicone-based resins). This is especially the case when it is desired to prepare a composition such as a nail varnish, a mascara, an eyeliner, a lip gloss or a hair composition such as a lacquer. The polymers can be dissolved or dispersed in the cosmetically acceptable medium and optionally combined with coalescing agents and/or plasticizers.

Examples of oils which can be used in the invention include: hydrocarbon-based oils of animal origin, such as perhydrosqualene; hydrocarbon-based plant oils such as liquid triglycerides of fatty acids of 4 to 10 carbon atoms, for instance heptanoic or octanoic acid triglycerides, or alternatively sunflower oil, corn oil, soybean oil, grapeseed oil, sesame oil, apricot oil, macadamia oil, castor oil, avocado oil, caprylic/capric acid triglycerides, jojoba oil, karite butter; linear or branched hydrocarbons of mineral or synthetic origin, such as liquid paraffins and derivatives thereof, petroleum jelly, polydecenes, hydrogenated polyisobutene such as parleam; synthetic esters and ethers, in particular of fatty acids or fatty alcohol containing from 8 to 26 carbon atoms, such as, for example, purcellin oil, isopropyl myristate, 2-ethylhexyl palmitate, 2-octyldodecyl stearate, 2-octyldodecyl erucate, isostearyl isostearate; hydroxylated fatty acid or fatty alcohol esters such as isostearyl lactate, octyl hydroxystearate, octyldodecyl hydroxystearate, diisostearyl malate, triisocetyl citrate, heptanoates, octanoates and decanoates of fatty alcohols; polyol esters such as propylene glycol dioctanoate, neopentyl glycol diheptanoate, diethylene glycol diisononanoate; and pentaerythritol esters; fatty alcohols containing from 12 to 26 carbon atoms, such as octyldodecanol, 2-butyloctanol, 2-hexyldecanol, 2-undecylpentadecanol, oleyl alcohol; partially hydrocarbon-based fluoro oils and/or silicone-based fluoro oils; silicone based oils such as volatile or non-volatile, linear or cyclic polymethylsiloxanes (PDMS) which are liquid or pasty at room temperature, such as cyclomethicones and dimethicones, optionally comprising a phenyl group, for instance phenyl trimethicones, phenyltrimethylsiloxydiphenylsiloxanes, diphenylmethyldimethyltrisiloxanes, diphenyl dimethicones, phenyl dimethicones, polymethylphenyl siloxanes; mixtures thereof.

These oils may represent from 0 to 99.99% by weight relative to the total weight of the fatty phase. This range includes all specific values and subranges therebetween, including 0.1, 0.2, 0.5, 1, 2, 5, 10, 25, 50, 75, 85, 90, 95, 98 and 99% by weight of the fatty phase.

The lipophilic continuous phase of the composition according to the invention can also comprise one or more cosmetically acceptable (acceptable tolerance, toxicology and feel) organic solvents. These organic solvents can represent from 0 to 90% of the total weight of the composition and can be chosen from the group consisting of lipophilic organic solvents, amphiphilic solvents and mixtures thereof. Examples of organic solvents which can be used in the composition of the invention include acetic acid esters such as methyl, ethyl, butyl, amyl or 2-methoxyethyl acetate; ketones such as methyl ethyl ketone, methyl isobutyl ketone, isopropyl acetate; hydrocarbons such as toluene, xylene, p-cylene, hexane or heptane; aldehydes containing from 5 to 10 carbon atoms; ethers containing at least 3 carbon atoms; and mixtures thereof.

The composition of the invention may also comprise an additional particulate phase which can be present in a proportion of from 0 to 30% of the total weight of the composition, preferably from 0.05 to 20%, and which can comprise pigments and/or pearlescent agents and/or fillers used in cosmetic compositions. These ranges include all specific values and subranges therebetween, such as 0.1, 0.2, 0.5, 1, 2, 5, 10, 15 and 25% by weight of the composition.

The term "pigments" should be understood as meaning white or colored, inorganic or organic particles which are insoluble in the liquid fatty phase and which are intended to color and/or opacify the composition. The term "fillers" should be understood as meaning colorless or white, inorganic or synthetic, lamellar or non-lamellar particles. The term "pearlescent agents" should be understood as meaning iridescent particles, in particular produced by certain molluscs in their shell or synthesized. These fillers and pearlescent agents serve in particular to modify the texture of the composition.

The pigments other than bismuth vanadate can be present in the composition in a proportion of from 0 to 25% of the weight of the final composition, and preferably in a proportion of from 2 to 15%. These ranges include all specific values and subranges therebetween such as 0.01, 0.02, 0.05, 1, 2, 5, 10 and 20% by weight of the composition. As inorganic pigments which can be used in the invention, mention may be made of titanium oxide, zirconium oxide or cerium oxide, as well as zinc oxide, iron oxide or chromium oxide and ferric blue. Among the organic pigments which can be used in the invention, mention may be made of carbon black and barium, strontium, calcium or aluminium lakes or alternatively the diketopyrrolopyrroles (DPP) described in EP-A-542,669, EP-A-787,730, EP-A-787,731 and WO 96/08537, each incorporated herein by reference.

The pearlescent agents can be present in the composition in a proportion of from 0 to 20% of the total weight of the composition, preferably in a content ranging from 1 to 15%. These ranges include all specific values and subranges therebetween, such as 0.01, 0.05, 1, 2, 5 and 10% by weight of the composition. Among the pearlescent agents which can be used in the invention, mention may be made of mica coated with titanium oxide, with iron oxide, with natural pigment or with bismuth oxychloride, such as colored titanium mica.

The fillers can be present in a proportion of from 0 to 30% of the total weight of the composition, preferably 0.5 to 15%. Preferred examples include talc, zinc stearate, mica, kaolin, Nylon (in particular Orgasol) powder, polyethylene powder, Teflon, starch, boron nitride, copolymer microspheres such as Expancel (Nobel Industrie), Polytrap (Dow Corning) and silicone resin microbeads (Tospearl from Toshiba, for example).

The composition of the invention can advantageously comprise a solid or pasty fatty phase containing one or more gums and/or one or more waxes and/or one or more pasty fatty substances. The waxes and the pasty fatty substances can be hydrocarbon-based waxes, fluoro waxes and/or silicone waxes and can be of plant, mineral, animal and/or synthetic origin. In particular, the waxes have a melting point of greater than 45° C. and the pasty fatty substances have melting points of from 25° C. to 45° C.

As waxes which can be used in the composition of the invention, mention may be made of beeswax, carnauba wax or candelilla wax, paraffin, microcrystalline waxes, ceresin or ozokerite; synthetic waxes such as polyethylene waxes or Fischer-Tropsch waxes, silicone waxes such as alkyl- or alkoxy-dimethicones containing from 16 to 45 carbon atoms.

The gums are generally high molecular weight PDMSs and the pasty substances are generally hydrocarbon-based compounds such as lanolins and derivatives thereof or alternatively PDMSs.

The nature and amount of the solid substances depend on the desired mechanical properties and textures. As a guide, the composition can contain from 0 to 50% by weight of waxes relative to the total weight of the composition, and preferably from 1 to 30%.

The composition according to the invention can furthermore comprise any ingredient conventionally used in the fields under consideration, and more especially in cosmetics and dermatology. These ingredients are chosen in particular for preserving agents, aqueous-phase thickeners (polysaccharide biopolymers, synthetic polymers) or fatty-phase thickeners, fragrances, hydrophilic or lipophilic active agents and mixtures thereof. The amounts of these various ingredients are those conventionally used in the fields under consideration, and, for example, from 0 to 20% and in particular from 0.01 to 15% of the total weight of the composition. The nature of these ingredients and their proportion must be compatible with the production of stable, thickened, glossy compositions according to the invention.

The composition can contain an aqueous, alcoholic or aqueous-alcoholic phase in dispersed or emulsified form in the continuous phase. This phase can contain water, alcohols or a mixture of water and alcohol or acetone. The alcohols are, in particular, linear or branched lower monoalcohols containing from 2 to 5 carbon atoms, such as ethanol or propanol, polyols such as glycerol, diglycerol, propylene glycol, sorbitol, pentenol, pentylene glycol or polyethylene glycols. This aqueous phase can represent from 0 to 70% of the weight of the composition. This aqueous phase may also contain $C_2$ ethers and $C_2$–$C_4$ aldehydes.

The composition according to the invention can have the appearance of a cream, salve, fluid lotion, soft paste with a dynamic viscosity at 25° C. ranging from 1 to 40 Pa.s, ointment, solid which is poured or cast and in particular as a stick or a dish.

This composition may be used for making up the skin and/or the lips and/or the superficial body growths depending on the nature of the constituents used. In particular, the composition of the invention can be a tube of lipstick or a lip lacquer, a lip gloss which can be used just as it is or for application to a film of lipstick in particular to increase its gloss and/or its color (known as a topcoat). It can also be a solid foundation, a concealer product or a product for the contours of the eyes, an eyeliner, a mascara, an eyeshadow, a compact powder, a blusher or a nail varnish. These compositions can also contain cosmetic or dermatological active agents, in particular in order to give the composition a care or treating appearance. Thus, the composition can contain vitamins and other lipophilic active agents (lanolin, UVA screening agent) or hydrophilic active agents (hydrating agents such as glycerol).

The present invention also includes a cosmetic use of the above composition to care for and/or make up and/or protect the skin and/or the lips and/or the superficial body growths of human beings, as well as a use of this composition for the preparation of an ointment intended to treat and/or protect the skin and/or the lips and/or the superficial body growths. A subject of the invention is also a cosmetic treatment process for the skin and/or the lips and/or the superficial body growths, which consists in applying the composition defined above to the skin and/or the lips and/or the superficial body growths of human beings.

More specifically, a subject of the invention is a lip product, a foundation or a nail varnish.

The composition of the invention can be obtained according to the preparation processes conventionally used in cosmetics or dermatology.

The present invention also includes the use, in a colored cosmetic composition or for the manufacture of a colored dermatological composition, of a coloring agent as described above, in order to protect the skin and/or the lips and/or the superficial body growths against the harmful effects of free radicals and/or to combat the signs of ageing, in particular photo-induced ageing, of the skin. These signs of ageing are, in particular, wrinkles, fine lines and flaccid and/or yellowed skin.

The present invention also relates to a process for the cosmetic protection of the skin and/or the lips and/or the superficial body growths against the harmful effects of free radicals and/or for combating the signs of photo-induced ageing of the skin, which consists in applying the composition as defined above to the skin and/or the lips and/or the superficial body growths.

EXAMPLES

Having generally described this invention, a further understanding can be obtained by reference to certain specific examples which are provided herein for purposes of illustration only and are not intended to be limiting unless otherwise specified. The percentages listed below are percentages by weight, unless noted otherwise.

Example 1

| W/O Type Foundation | |
|---|---|
| Composition | |
| cyclopentasiloxane | 25.05% |
| dimethicone copolyol in cyclopentasiloxane* | 6.00% |
| isododecane | 4.55% |
| pigments | |
| red-brown iron oxide | 0.67% |
| black iron oxide | 0.25% |
| titanium dioxide | 7.63% |
| bismuth vanadate (Sicopal Yellow L1100) | 0.75% |
| nylon powder | 8.00% |
| fragrance | 0.60% |
| magnesium silicate | 0.60% |
| cellulose gum | 3.50% |
| isostearyl diglyceryl succinate | 2.00% |
| water | qs 100% |

Procedure

The pigments are predispersed in the mixture of cyclomethicones and the fatty phase (surfactants+oils) is then homogenized at 40°–50° C. This mixture is left to cool and the predispersed pigments are then added. All the pre-homogenized aqueous phase is incorporated into the fatty phase with stirring. Moderate stirring is maintained until the mixture has emulsified.

A beige-colored foundation which has high covering power, is stable to light and leaves no scratches (or marks) after removal of the make-up is obtained.

Example 2

Anhydrous Lipstick

| Composition | |
|---|---|
| esters of $C_8$–$C_{10}$ fatty alcohols | 30.0% |
| $C_{10}$ fatty alcohol | 7.0% |
| aluminium starch octylsuccinate | 10.0% |
| ozokerite | 10.0% |
| carnauba wax | 4.0% |
| beeswax | 3.0% |
| titanium dioxide | 3.0% |
| bismuth vanadate (Sicopal Yellow L1100) | 1.0% |
| Flaming Red (C12085) | 1.0% |
| fragrance | 0.5% |
| castor oil | qs 100% |

Procedure

The pigments are ground in the mixture of fatty alcohols, fatty alcohol esters and castor oil. The ozokerite, the carnauba wax and the beeswax are melted at the time of use in a container and are introduced into the mixture with continuous stirring. The aluminium starch octylsuccinate is introduced under vacuum and finally the fragrance is incorporated. The mixture is cast in a suitable mould in order to obtain a stick and is then left to cool to room temperature.

A stable, orange-colored lipstick which covers well is obtained.

Example 3

Anhydrous Nail Varnish

| Composition | |
|---|---|
| nitrocellulose | 10.9% |
| toluene sulphonamide formaldehyde resin (Ketjenflex MS80 sold by AKZO) | 10.7% |
| acetyl tributyl citrate (Citroflex A4 sold by Pfizer) | 6.5% |
| toluene | 31.0% |
| butyl acetate | 21.6% |
| ethyl acetate | 9.3% |
| isopropyl alcohol | 7.7% |
| stearalkonium hectorite | 1.3% |
| bismuth vanadate (Sicopal Yellow L1100) | 1.0% |
| citric acid | 0.1% |

Procedure:

All the constituents of the composition are mixed together at room temperature.

A glossy, bright yellow nail varnish which is stable to light is obtained.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 98-14160, filed on Nov. 10, 1998, and incorporated herein by reference in its entirety.

What is claimed is:

1. A colored composition suitable for topical application, comprising a lipophilic continuous phase and an amount of bismuth vanadate effective to color the composition.

2. The composition of claim 1, containing a pigment in an amount of from 0.01 to 50% by weight relative to the weight of the composition.

3. The composition of claim 1, containing a pigment in an amount of from 0.5 to 25% by weight relative to the weight of the composition.

4. The composition of claim 1, which is in the form of a make-up product for the skin, the lips and/or the superficial body growths of a human being.

5. The composition of claim 1, which is in the form of a mascara, eyeliner, hair composition such as a lacquer, lip product, lip gloss, foundation, concealer product, face powder, eyeshadow, body make-up, powders or nail varnish.

6. The composition of claim 1, wherein the fatty continuous phase contains at least one fatty substance selected from the group consisting of oils, waxes, gums, pasty fatty substances, lipophilic organic solvents and mixtures thereof.

7. The composition of claim 1, further comprising at least one aqueous, alcoholic or aqueous-alcoholic phase dispersed or emulsified in the lipophilic phase.

8. The composition of claim 1, wherein the bismuth vanadate is present in a particulate phase.

9. The composition of claim 1, further comprising an additional particulate phase which comprises more than 0 up to 30% of the total weight of the composition.

10. The composition of claim 1, which is in the form of an emulsion or a dispersion in an oily or waxy phase or a lipophilic organic solvent, anhydrous gel or anhydrous paste.

11. A method of preparing the composition of claim 1, comprising combining the lipophilic continuous phase and the bismuth vanadate.

12. A method of caring for the skin and/or the lips and/or the superficial body growths comprising, applying the composition of claim 1 to the skin and/or the lips and/or the superficial body growths.

13. A method of making up the skin and/or the lips and/or the superficial body growths, comprising applying the composition of claim 1 to the skin and/or the lips and/or the superficial body growths.

14. A method of protecting the skin and/or the lips and/or the superficial body growths, comprising applying the composition of claim 1 to the skin and/or the lips and/or the superficial body growths.

15. A method of protecting the skin and/or the lips and/or the superficial body growths against the harmful effects of free radicals, comprising applying the composition of claim 1 to the skin and/or the lips and/or the superficial body growths.

16. A method of alleviating the signs of ageing of the skin, comprising applying the composition of claim 1 to the skin.

* * * * *